(12) United States Patent
Suyama et al.

(10) Patent No.: US 12,028,597 B2
(45) Date of Patent: Jul. 2, 2024

(54) IMAGE PICKUP APPARATUS AND ENDOSCOPE

(71) Applicant: OLYMPUS CORPORATION, Tokyo (JP)

(72) Inventors: Takuro Suyama, Ina (JP); Ken Yamamoto, Nagano (JP); Takatoshi Igarashi, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/868,929

(22) Filed: Jul. 20, 2022

(65) Prior Publication Data

US 2022/0368816 A1 Nov. 17, 2022

Related U.S. Application Data

(63) Continuation of application No. PCT/JP2020/002758, filed on Jan. 27, 2020.

(51) Int. Cl.
H04N 23/54 (2023.01)
A61B 1/04 (2006.01)
(Continued)

(52) U.S. Cl.
CPC ............... *H04N 23/54* (2023.01); *A61B 1/04* (2013.01); *A61B 1/051* (2013.01); *H04N 23/555* (2023.01)

(58) Field of Classification Search
CPC ...... H04N 23/54; H04N 23/555; H04N 23/52; H04N 25/70; A61B 1/04; A61B 1/051;
(Continued)

(56) References Cited

U.S. PATENT DOCUMENTS

2010/0102428 A1* 4/2010 Lee ..................... H01L 25/0657
257/E25.013
2011/0233702 A1* 9/2011 Takahashi ......... H01L 27/14638
257/E31.127
(Continued)

FOREIGN PATENT DOCUMENTS

EP 3 369 360 A1 9/2018
EP 3 369 363 A1 9/2018
(Continued)

OTHER PUBLICATIONS

International Search Report dated Apr. 14, 2020 received in PCT/JP2020/002758.

*Primary Examiner* — Nasim N Nirjhar
(74) *Attorney, Agent, or Firm* — Scully, Scott, Murphy & Presser, P.C.

(57) ABSTRACT

An image pickup apparatus includes a stacked device in which a plurality of semiconductor devices respectively including a plurality of through electrodes are stacked, a first semiconductor device, among the plurality of semiconductor devices, in which thermal resistance of a through electrode is highest among the plurality of through electrodes, is disposed in front of a first surface on which a first circuit that is one of the semiconductor circuits having a largest heat generation amount is formed, the plurality of through electrodes of the first semiconductor device are conformal vias, and the plurality of through electrodes of semiconductor devices other than the first semiconductor device are filled vias.

15 Claims, 7 Drawing Sheets

(51) Int. Cl.
*A61B 1/05* (2006.01)
*H04N 23/50* (2023.01)

(58) Field of Classification Search
CPC ... A61B 1/0011; A61B 1/128; H01L 21/3205; H01L 21/768; H01L 23/522; H01L 25/065; H01L 25/07; H01L 25/18; H01L 27/146
See application file for complete search history.

(56) References Cited

U.S. PATENT DOCUMENTS

| | | |
|---|---|---|
| 2013/0010145 A1 | 1/2013 | Hagiwara et al. |
| 2014/0016270 A1 | 1/2014 | Bonkohara |
| 2014/0218573 A1 | 8/2014 | Hagiwara et al. |
| 2014/0316198 A1* | 10/2014 | Krivopisk ......... A61B 1/00181 600/109 |
| 2015/0123234 A1 | 5/2015 | Hagiwara et al. |
| 2017/0250141 A1* | 8/2017 | Imayoshi ................ H05K 1/11 |
| 2018/0220879 A1 | 8/2018 | Igarashi et al. |
| 2018/0303325 A1* | 10/2018 | Fujimori ................ A61B 1/04 |
| 2018/0310813 A1 | 11/2018 | Igarashi |
| 2018/0325364 A1* | 11/2018 | Okamura ............... H04N 25/70 |
| 2021/0035874 A1* | 2/2021 | Kudo ..................... H01L 23/145 |

FOREIGN PATENT DOCUMENTS

| | | |
|---|---|---|
| JP | 2004-006564 A | 1/2004 |
| JP | 2008-193358 A | 8/2008 |
| JP | 2010-050259 A | 3/2010 |
| JP | 2012-142458 A | 7/2012 |
| JP | 2013/021031 A | 1/2013 |
| JP | 2013-030593 A | 2/2013 |
| JP | 2013-187361 A | 9/2013 |
| JP | 2013/201568 A | 10/2013 |
| JP | 2017-079240 A | 4/2017 |
| JP | 2018/085353 A | 5/2018 |
| WO | 2012/091140 A1 | 7/2012 |
| WO | 2017/057291 A1 | 4/2017 |
| WO | 2017/072847 A1 | 5/2017 |
| WO | 2017/072862 A1 | 5/2017 |
| WO | 2017/073440 A1 | 5/2017 |
| WO | 2018/092318 A1 | 5/2018 |
| WO | 2018/193531 A1 | 10/2018 |
| WO | 2018/194039 A1 | 10/2018 |
| WO | 2019/138442 A1 | 7/2019 |
| WO | 2019/138737 A1 | 7/2019 |

* cited by examiner

IMAGE PICKUP APPARATUS AND ENDOSCOPE

CROSS REFERENCE TO RELATED APPLICATION

This application is a continuation application of PCT/JP2020/002758 filed on Jan. 27, 2020, the entire contents of which are incorporated herein by this reference.

BACKGROUND OF THE INVENTION

1. Field of the Invention

The present invention relates to an image pickup apparatus including a stacked device, and an endoscope that includes the image pickup apparatus including the stacked device.

2. Description of the Related Art

An image pickup signal outputted by an image pickup apparatus disposed at a distal end portion of an endoscope is processed by a plurality of electronic components and transmitted.

Japanese Patent Application Laid-Open Publication No. 2013-30593 discloses a stacked device in which a plurality of semiconductor devices are stacked to store a plurality of electronic components in a small space and to reduce parasitic capacitance due to wiring.

International Publication No. 2017/073440 discloses an endoscope that achieves a smaller size and higher functionality of an image pickup apparatus by bonding a plurality of semiconductor devices to a rear surface of an image pickup device.

SUMMARY OF THE INVENTION

An image pickup apparatus of an embodiment includes a stacked device in which a plurality of semiconductor devices respectively including a plurality of through electrodes are stacked, wherein the plurality of semiconductor devices include an image pickup device and circuit devices which are disposed behind the image pickup device and in which semiconductor circuits are respectively formed, a first semiconductor device, among the plurality of semiconductor devices, in which thermal resistance of a through electrode is highest among the plurality of through electrodes, is disposed in front of a first surface on which a first circuit that is one of the semiconductor circuits having a largest heat generation amount is formed, the plurality of through electrodes of the first semiconductor device are conformal vias, and the plurality of through electrodes of semiconductor devices other than the first semiconductor device are filled vias.

An endoscope of an embodiment includes an image pickup apparatus, the image pickup apparatus including a stacked device in which a plurality of semiconductor devices are stacked, the plurality of semiconductor devices respectively include a plurality of through electrodes, the plurality of semiconductor devices include an image pickup device, and circuit devices which are disposed behind the image pickup device and in which semiconductor circuits are respectively formed, a first semiconductor device, among the plurality of semiconductor devices, in which thermal resistance of a through electrode is highest among the plurality of through electrodes, is disposed in front of a first surface on which a first circuit that is one of the semiconductor circuits having a largest heat generation amount is formed, the plurality of through electrodes of the first semiconductor device are conformal vias, and the plurality of through electrodes of semiconductor devices other than the first semiconductor device are filled vias.

DETAILED DESCRIPTION OF THE PREFERRED EMBODIMENTS

<Configuration of Endoscope>

Figure 1:
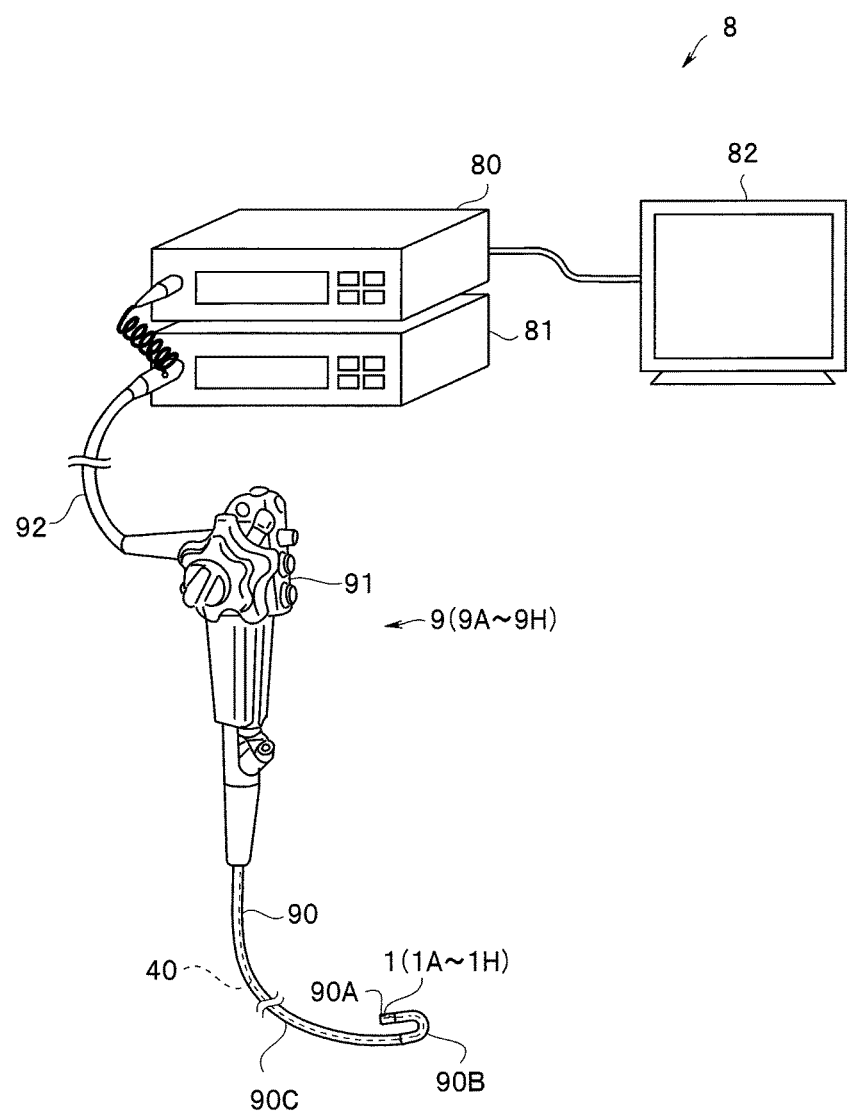
FIG. 1 is an appearance diagram of an endoscope of embodiments.

An endoscope system 8 illustrated in FIG. 1 includes an endoscope 9 of the present embodiment, a processor 80, a light source apparatus 81, and a monitor 82. The endoscope 9 includes an insertion portion 90, an operation portion 91 and a universal cord 92. The endoscope 9 photographs inside of a body of a subject by the insertion portion 90 being inserted into a body cavity of the subject, and outputs an image signal.

The insertion portion 90 is constituted with a distal end portion 90A at which an image pickup apparatus 1 is disposed, a bending portion 90B which is disposed continuously from the distal end portion 90A and which can freely bend, and a flexible portion 90C that is disposed continuously from the bending portion 90B. The bending portion 90B bends by operation of the operation portion 91.

At a proximal end portion of the insertion portion 90 of the endoscope 9, the operation portion 91 at which various kinds of buttons for operating the endoscope 9 are provided is disposed.

The light source apparatus 81 includes, for example, a white LED. Illumination light emitted by the light source apparatus 81 is guided to the distal end portion 90A by way of a light guide (not illustrated) that passes through the universal cord 92 and the insertion portion 90 and illuminates the subject.

The universal cord 92 is connected to the processor 80 by way of a connector. The processor 80, which controls the whole of the endoscope system 8, performs signal processing on an image pickup signal outputted by the image pickup apparatus 1 and outputs a result as an image signal. The monitor 82 displays the image signal outputted by the processor 80 as an endoscope image.

As will be described later, the image pickup apparatus 1 is small and has high reliability because heat effect from the stacked semiconductor devices to an image pickup device can be reduced. Thus, the endoscope 9 has high reliability and is less-invasive because the distal end portion 90A has a small diameter.

Note that while the endoscope 9 is a medical flexible endoscope, the endoscope of the present invention may be a rigid endoscope or may be intended for industrial use. The endoscope 9 may be an industrial endoscope in which the insertion portion 90 is directly connected to the monitor 82.

First Embodiment

Figure 2:
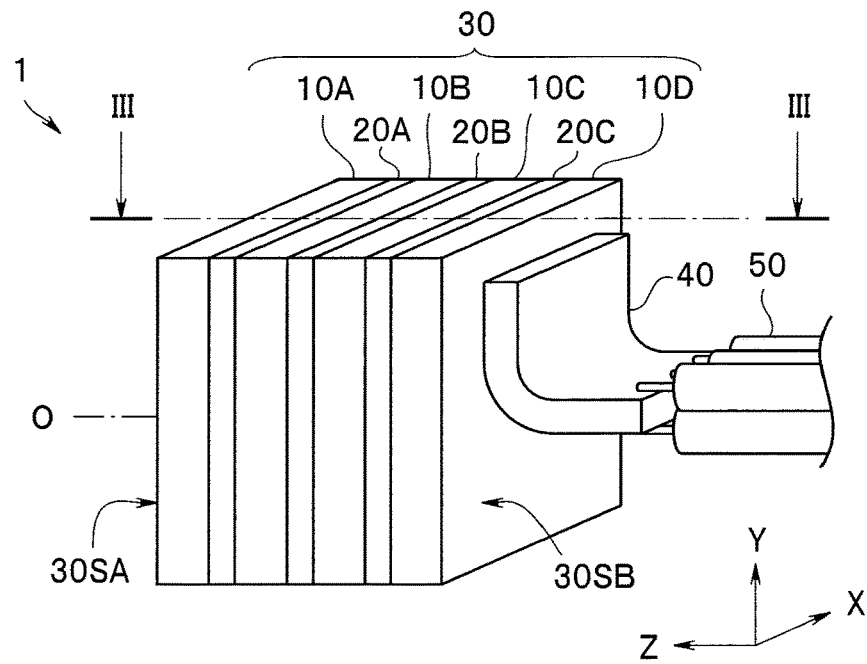
FIG. 2 is a perspective view of an image pickup apparatus of a first embodiment.
Figure 3:
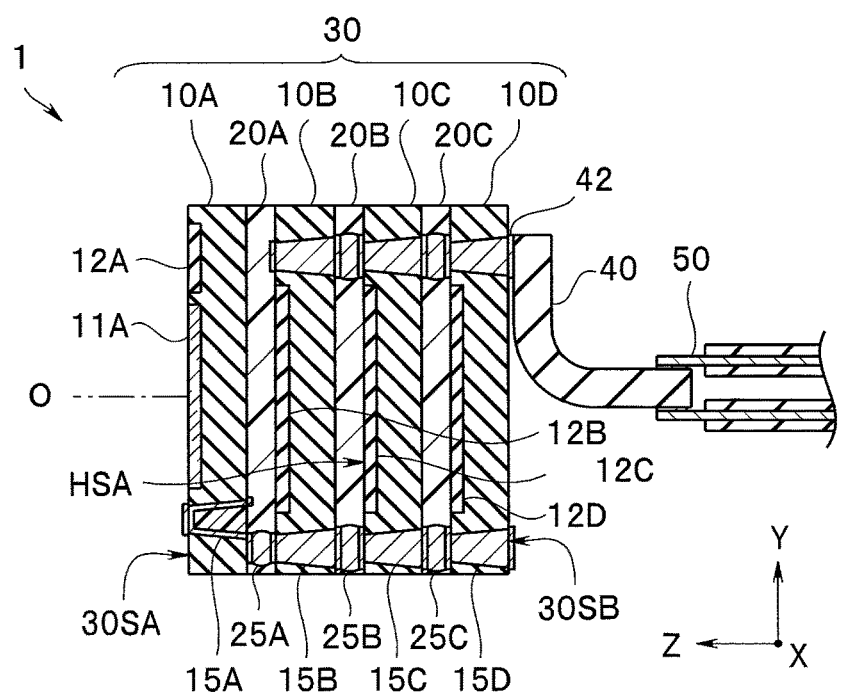
FIG. 3 is a cross-sectional view of the image pickup apparatus of the first embodiment along a line III-III in FIG. 2.

The image pickup apparatus 1 of the present embodiment illustrated in FIG. 2 and FIG. 3 includes a stacked device 30, a wiring board 40 and a signal cable 50.

Note that the drawings based on the respective embodiments are schematically illustrated. Relationships between thickness and width of each portion, ratios, relative angles, and the like, of each portion are different from actual relationships, ratios, relative angles, and the like. There are portions in which relationships of dimensions and ratios are different among the drawings. Further, illustration and assignment of reference numerals of some components are omitted. Still further, a direction in which an image of a subject is to be picked up will be referred to as "front", and a direction opposite to "front" will be referred to as "rear".

The stacked device 30 including a front surface 30SA and a rear surface 30SB that is an opposite side of the front surface 30SA has a substantially rectangular parallelepiped shape in which an image pickup device 10A disposed in a forefront, and a plurality of circuit devices 10B, 10C and 10D disposed behind the image pickup device 10A are stacked. All of the image pickup device 10A and the circuit devices 10B, 10C, and 10D are semiconductor devices including silicon substrates.

The image pickup device (imager) 10A includes, for example, a light reception circuit 11A and a peripheral circuit 12A including a CCD or a CMOS on the front surface 30SA. The light reception circuit 11A, and the like, are connected to a plurality of through electrodes 15A. The image pickup device 10A may be either a front side illumination image sensor or back side illumination image sensor. While not illustrated, a cover glass and an image pickup optical system are disposed on the front surface 30SA.

At the circuit devices 10B, 10C and 10D, semiconductor circuits 12B, 12C and 12D are respectively formed. The circuit devices 10B, 10C, and 10D respectively include a plurality of through electrodes 15B, 15C and 15D. Note that while the through electrodes 15A to 15D have a circular cross-sectional shape orthogonal to an optical axis O, the through electrodes may have a rectangular cross-sectional shape.

The semiconductor circuits 12B, 12C and 12D process the image pickup signal outputted by the image pickup device 10A and processes a control signal for controlling the image pickup device 10A. The circuit devices 10B to 10D include, for example, an AD conversion circuit, a memory, a transmission output circuit, a drive signal generation circuit, a filter circuit, a thin film capacitor and a thin film inductor. A plurality of semiconductor circuits may be formed in one circuit device, or semiconductor circuits may be respectively formed on both principal surfaces of one circuit device.

While in the image pickup apparatus 1, the stacked device 30 includes four semiconductor devices (the image pickup device 10A and the circuit devices 10B to 10D), the present invention is not limited to the configuration. The number of semiconductor devices included in the stacked device 30 only requires to be equal to or larger than two including the image pickup device 10A, and is, for example, preferably equal to or larger than two and equal to or less than ten.

The image pickup device 10A and the circuit devices 10B to 10D are respectively stacked with intermediate layers 20A to 20C respectively including bonding conductors 25A to 25C being put between the image pickup device 10A and the circuit devices 10B to 10D. The intermediate layers 20A to 20C respectively include sealing resin and the bonding conductors 25A to 25C that electrically connects the image pickup device 10A and the circuit devices 10B to 10D.

The intermediate layers 20A to 20C may include air or an inert gas in place of the sealing resin. However, the intermediate layers 20A to 20C preferably include sealing resin in terms of improvement in durability of the stacked device 30.

As the sealing resin, for example, epoxy resin, polyimide resin, fluorine resin, polyamide imide, polyphenylene ether, polypropylene, polysulfone, poly ether sulfone, poly ether ether ketone, poly ether ketone, poly ether imide, thermoplastic elastomer fluorine, butadiene rubber, or the like, can be used.

The bonding conductors 25A to 25C are, for example, constituted with a solder bump by an electroplating method, a solder paste film by printing, or the like, and a stud bump formed with gold. The bonding conductor constituted with solder bonds two electrodes through thermal bonding or thermal ultrasonic bonding in which heat is applied along with application of ultrasound. The bonding conductor formed with gold bonds two electrodes through ultrasonic bonding.

For example, the stacked device 30 is manufactured by the circuit devices 10B to 10D being solder-bonded to each other by the bonding conductors 25B and 25C constituted with solder, and the circuit device 10B and the image pickup device 10A being ultrasonic bonded by the bonding conductor 25A formed with gold.

The signal cable 50 is electrically connected to the circuit device 10D.

In the image pickup apparatus 1, one end of the wiring board 40 is bonded to a bonding electrode 42 on the rear surface 30SB, and the signal cable 50 is bonded to the other end of the wiring board 40. For example, one end of the wiring board 40 is solder-bonded to the bonding electrode 42 which is formed with barrier nickel and gold and which is disposed in a wiring pattern formed with copper on the rear surface 30SB. Note that the image pickup apparatus 1 does not have to include the wiring board 40, and the signal cable 50 may be directly bonded to the bonding electrode 42 of the stacked device 30. Further, while in the illustrated drawing, the wiring board 40 is a flexible wiring board, the wiring board 40 is not limited to the flexible wiring board and may be a rigid wiring board or a MID (molded interconnect device).

The semiconductor circuits 12B to 12D generate heat in accordance with power consumption of the semiconductor circuits 12B to 12D. A "circuit with a largest heat generation amount" in the present invention refers to a "circuit with largest power consumption".

In the image pickup apparatus 1, a first semiconductor device in which the through electrode 15A has highest thermal resistance (high heat resistant device) among the four semiconductor devices (the image pickup device 10A and the circuit devices 10B to 10D) is the image pickup device 10A. Further, the image pickup device 10A is disposed in front of a first surface (heat generation surface) HSA of the circuit device 10C on which the semiconductor circuit 12C that is a first circuit (heat generation circuit) with the largest heat generation amount is formed.

Here, thermal resistance is a parameter that indicates a degree of difficulty of heat transfer from one end to the other end of a heat transfer path. For example, the thermal resistance of the through electrodes can be compared by comparing materials of conductors included in the through electrodes and heat transfer paths. For example, as heat conductivity of a material of a conductor included in a through electrode is lower, thermal resistance becomes higher, and as a diameter of the conductor, that is, a cross-section area of a heat transfer path is smaller, the thermal resistance becomes higher.

In other words, the image pickup device 10A including the through electrode 15A having the highest thermal resistance among the through electrodes 15A to 15D is disposed in front of the first surface HSA in which the semiconductor circuit 12C that is the first circuit having the largest heat generation amount is formed.

Figure 4A:
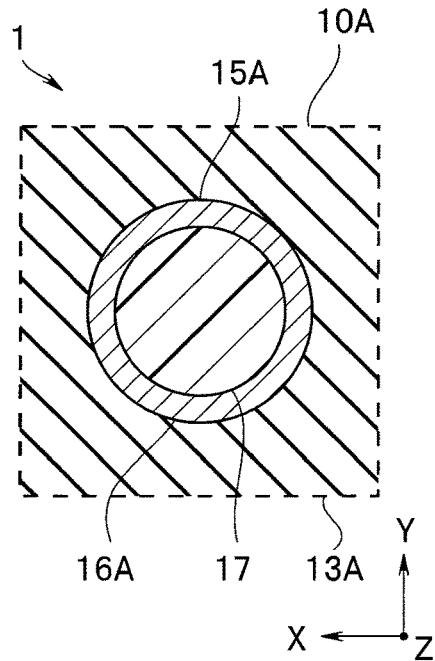
FIG. 4A is a cross-sectional view of the image pickup apparatus of the first embodiment in a direction orthogonal to an optical axis of a conformal via.
Figure 4B:
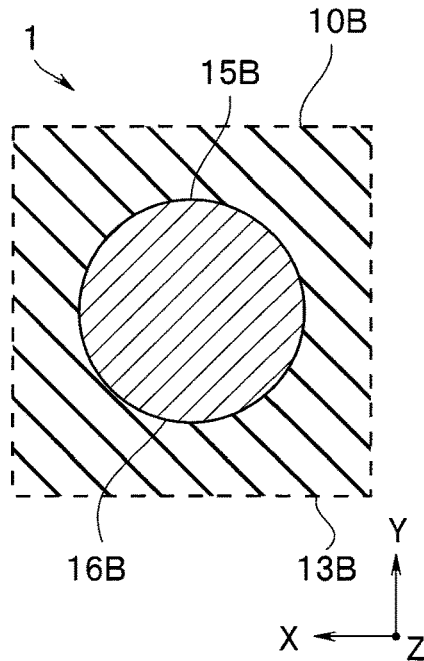
FIG. 4B is a cross-sectional view of the image pickup apparatus of the first embodiment in a direction orthogonal to an optical axis of a filled via.

The through electrode 15A of the image pickup device 10A illustrated in FIG. 4A is a conformal via in which the conductor 16A is disposed on a wall surface of a through hole via of a substrate 13A and a central portion surrounded by the conductor 16A is filled with resin 17. In contrast, the through electrode 15B of the circuit device 10B illustrated in FIG. 4B is a filled via in which a through hole via of a substrate 13B is filled with a conductor 16B. The circuit devices 10C and 10D are also constituted in a similar manner.

As described above, all the image pickup device 10A and the circuit devices 10B to 10D include silicon substrates, and a thickness of the image pickup device 10A is equal to or greater than 80% and equal to or less than 120% of thicknesses of the circuit devices 10B to 10D, which are substantially the same, and thus, the thermal resistance of the substrates is substantially the same. Further, the image pickup device 10A and the circuit devices 10B to 10D include substantially the same number of through electrodes having substantially the same external size (cross-section area).

Heat conductivity of the conductor 16 of the through electrode 15A is higher than heat conductivity (160 W/m·K) of silicon that is a material of the substrate (for example, heat conductivity of copper that is the conductor 16 is 400 W/m·K). Further, heat conductivity of the resin 17 is lower than heat conductivity of silicon that is the material of the substrate (for example, heat conductivity of epoxy resin that is the resin 17 is 0.35 W/m·K). Thus, a main heat transfer path of the semiconductor device is the conductor of the through electrode.

The through electrode 15A of the image pickup device 10A has a smaller cross-section area of the conductor 16A having high heat conductivity than a cross-section area of the conductors of the through electrodes 15B to 15D and includes the resin 17 having low heat conductivity. Thus, thermal resistance of the through electrode 15A is higher than thermal resistance of the through electrodes 15B to 15D.

However, in the image pickup device 10A, a cross-section area parallel to the front surface 30SA of the conductor 16A of the through electrode 15A, that is, a cross-section area of a heat transfer path, that is a cross-section area of the conductor 16A of the through electrode 15A in a cross-section parallel to a planar direction at the center in a thickness direction, is smaller than the cross-section areas of the conductors of the through electrodes of the circuit devices 10B to 10D.

The thermal resistance of the through electrode 15A of the image pickup device 10A is high, and thus, heat generated from the semiconductor circuit 12C that is the first circuit with the largest heat generation amount is more transferred to the wiring board 40 and is less transferred to the light reception circuit 1A. In other words, the heat generated from the semiconductor circuit 12C is more transferred to the signal cable 50 by way of the wiring board 40. The image pickup apparatus 1 is small and has high reliability because heat effect from the circuit devices 10B to 10D to the image pickup device 10A that are stacked can be reduced.

Note that it is much preferable that a material of the conductor 16A of the through electrode 15A of the image pickup device 10A have heat conductivity smaller than heat conductivity of copper that is a material of conductors of the through electrodes 15B to 15C. It is much preferable that, for example, aluminum (heat conductivity: 236 W/m·K) or gold (heat conductivity: 319 W/m·K) be used as the conductor 16A of the through electrode 15A.

Further, while in the image pickup apparatus 1, the first semiconductor device in which the through electrodes have the highest thermal resistance is the image pickup device 10A, and the first circuit with the largest heat generation amount is the semiconductor circuit 12C, the first semiconductor device and the first circuit are not respectively limited to the image pickup device 10A and the semiconductor circuit 12C. In other words, the first semiconductor device only requires to be disposed in front of a surface on which the first circuit is formed, and the circuit devices 10B to 10D may be first semiconductor devices, and the semiconductor circuits 12B and 12D may be the first circuits.

Modifications of First Embodiment

Image pickup apparatuses 1A to 1C of modifications of the first embodiment are similar to the image pickup apparatus 1, and thus, the same reference numerals will be assigned to components having the same functions, and description will be omitted.

Modification 1 of First Embodiment

Figure 5A:
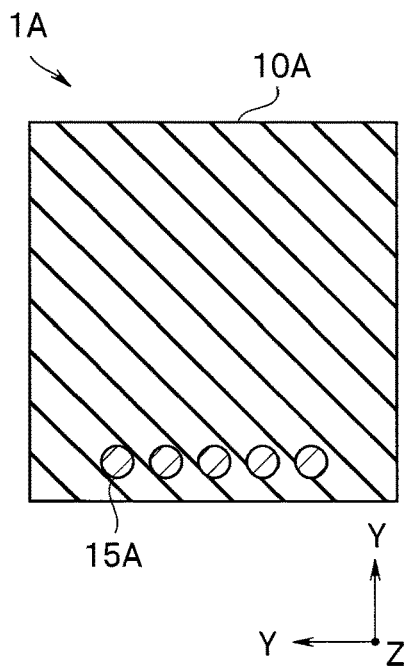
FIG. 5A is a cross-sectional view of an image pickup apparatus of modification 1 of the first embodiment in a direction orthogonal to an optical axis of an image pickup device.
Figure 5B:
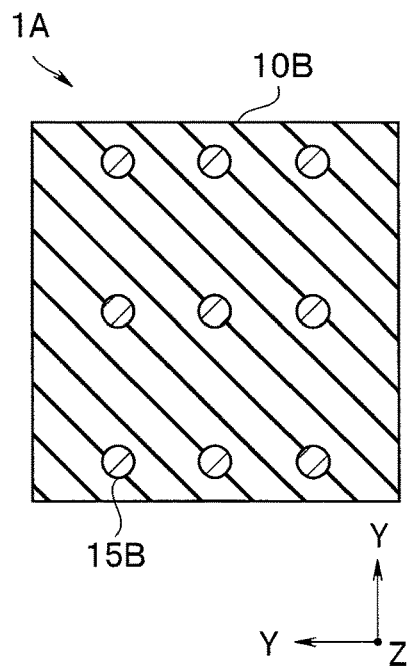
FIG. 5B is a cross-sectional view of the image pickup apparatus of modification 1 of the first embodiment in a direction orthogonal to an optical axis of a circuit device.

In the image pickup apparatus 1A of the present modification illustrated in FIG. 5A and FIG. 5B, the through electrode 15A of the image pickup device 10A is a filled via having substantially the same size (cross-section area) as a size of the through electrodes 15B to 15D of the circuit devices 10B to 10D. However, while the image pickup device 10A includes five through electrodes 15A, the circuit devices 10B to 10D each include nine through electrodes 15B to 15D.

A sum of cross-section areas of the conductors 16 of the plurality of through electrodes of the image pickup device 10A, on a cross-section parallel to the front surface 30SA is smaller than a sum of cross-section areas of the conductors of the plurality of through electrodes of the circuit devices 10B, 10C and 10D. Thus, the image pickup device 10A is the first semiconductor device having higher thermal resistance than thermal resistance of the circuit devices 10B, 10C and 10D.

In the image pickup apparatus 1A, the image pickup device 10A is the first semiconductor device having higher thermal resistance than the thermal resistance of the circuit devices 10B, 10C and 10D, and thus, there is no possibility of degradation of image quality or reliability.

Note that it goes without saying that even if the number of the through electrodes is the same, thermal resistance of the semiconductor device changes in accordance with a sum of cross-section areas of the conductors of the through electrodes. In other words, even if the image pickup device 10A includes through electrodes of the same number as the number of through electrodes of the circuit devices 10B, 10C and 10D, if a sum of cross-section areas of the conductors is smaller than a sum of cross-section areas of the conductors of the circuit devices 10B, 10C and 10D, the thermal resistance becomes higher than thermal resistance of the circuit devices 10B, 10C and 10D.

Modification 2 of First Embodiment

Figure 6:
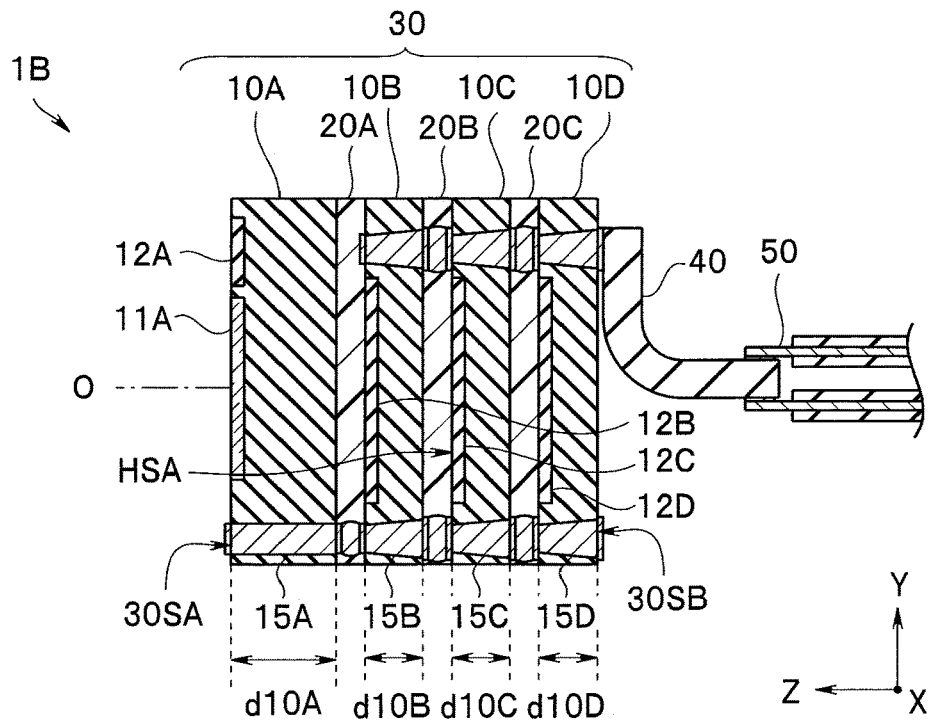
FIG. 6 is a cross-sectional view of an image pickup apparatus of modification 2 of the first embodiment.

In the image pickup apparatus 1B of the present modification illustrated in FIG. 6, the image pickup device 10A has a substrate thicker than substrates of the circuit devices 10B, 10C and 10D. In other words, a thickness d10A of the substrate of the image pickup device 10A is over 120% of thicknesses d10B, d10C and d10F of the circuit devices 10B, 10C and 10D, and thus, the heat transfer path is long. Thus, the image pickup device 10A is the first semiconductor device having higher thermal resistance than the thermal resistance of the circuit devices 10B, 10C and 10D.

In the image pickup apparatus 1B, the image pickup device 10A is the first semiconductor device having higher thermal resistance than the thermal resistance of the circuit devices 10B, 10C and 10D, and thus, there is no possibility of degradation of image quality or reliability.

If the image pickup device 10A becomes the first semiconductor device by at least one of a configuration of the image pickup device 10A in which the through electrode 15A of the image pickup device 10A is a conformal via and the through electrodes 15B to 15D of the circuit devices 10B to 10D are filled vias, a configuration of the image pickup apparatus 1A in which the number of the through electrodes 15A is smaller than the number of the through electrodes 15B to 15D, or a configuration of the image pickup apparatus 1B in which the thickness d10A of the substrate of the image pickup device 10A is greater than the thicknesses d10B, d10C and d10F of the circuit devices 10B to 10D, there is no possibility of degradation of image quality or reliability.

Note that the circuit device 10B disposed in front of the first surface HSA may be the first semiconductor device in which the through electrodes have the highest thermal resistance.

Modification 3 of First Embodiment

Figure 7:
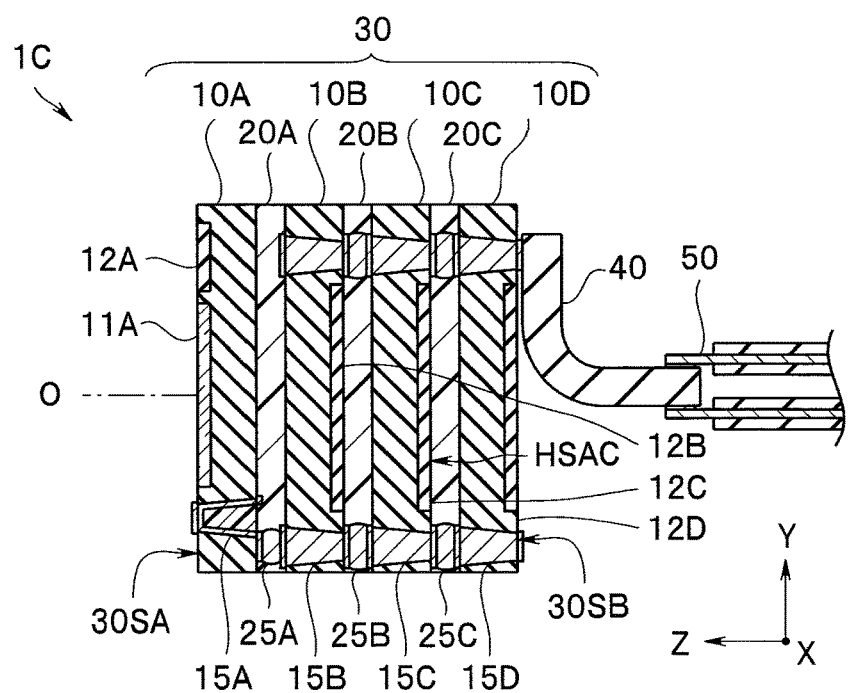
FIG. 7 is a cross-sectional view of an image pickup apparatus of modification 3 of the first embodiment.

In the image pickup apparatus 1C of the present modification illustrated in FIG. 7, a rear surface of the circuit device 10C on which the semiconductor circuit 12C that is the first circuit having the largest heat generation amount is formed is a first surface HSAC. Thus, in the image pickup apparatus 1C, heat generated from the semiconductor circuit 12C is less transferred to the image pickup device 10A and is more transferred to the signal cable 50 compared to an image pickup apparatus in which the first circuit is formed on a front surface of the circuit device 10C.

The heat generated from the semiconductor circuit 12C that is the first circuit is more transferred to the wiring board 40 and is less transferred to the light reception circuit 11A. Thus, there is no possibility of degradation of image quality or reliability due to thermal noise in the image pickup apparatus 1C.

Further, it is preferable that the image pickup device 10A and the circuit devices 10B and 10C disposed in front of the first surface HSAC have higher thermal resistance than thermal resistance of the circuit device 10D disposed behind the first surface HSAC, because the heat generated from the semiconductor circuit 12C is more transferred to the wiring board 40 and is less transferred to the light reception circuit 11A.

Still further, it is preferable that the image pickup device 10A and the circuit devices 10B and 10C disposed in front of the first surface HSAC have higher thermal resistance as the device is disposed further toward the front, because the heat generated from the semiconductor circuit 12C is less transferred to the light reception circuit 11A.

Second Embodiment

An image pickup apparatus 1D of a second embodiment is similar to the image pickup apparatus 1, and thus, the same reference numerals will be assigned to components having the same functions, and description will be omitted.

Figure 8:
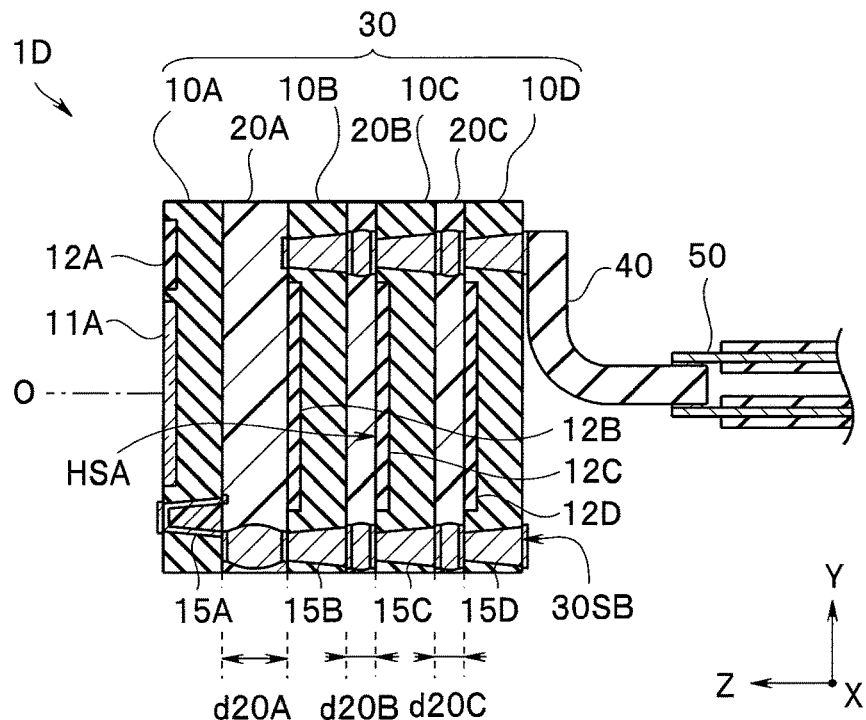
FIG. 8 is a cross-sectional view of an image pickup apparatus of a second embodiment.

In the image pickup apparatus 1D illustrated in FIG. 8, the intermediate layer 20A disposed between the image pickup device 10A and the circuit device 10B closest to the front surface 30SA is a first layer (heat shield layer) having the highest thermal resistance among the intermediate layers 20A to 20C. In other words, the first layer (intermediate layer 20A) having the highest thermal resistance is disposed between the first surface HSA and the front surface 30SA.

In the intermediate layers 20A to 20C, portions around the bonding conductors 25A, 25B and 25C constituted through solder are filled with sealing resin, for example, constituted with epoxy resin having heat conductivity of 0.35 W/m·K.

A thickness d20A of the intermediate layer 20A is over 150% of a thickness d20B of the intermediate layer 20B and a thickness d20C of the intermediate layer 20C. Thus, the intermediate layer 20A has higher thermal resistance than thermal resistance of the intermediate layers 20B and 20C.

Heat generated from the semiconductor circuit 12C that is the first circuit is more transferred to the wiring board 40 and is less transferred to the light reception circuit 11A because thermal resistance of the heat transfer path to the wiring board 40 is small. Thus, there is no possibility of degradation of image quality or reliability due to thermal noise in the image pickup apparatus 1D.

Note that the intermediate layer 20B may be the first layer having the highest thermal resistance. In other words, the heat generated from the semiconductor circuit 12C that is the first circuit is less transferred to the image pickup device 10A if the first layer having the highest thermal resistance among the plurality of intermediate layers is disposed between the first surface HSA and the front surface 30SA.

Further, in the image pickup apparatus 1D illustrated in FIG. 8, the through electrode 15A of the image pickup device 10A is a conformal via, and the through electrodes 15B, 15C and 15D of the circuit devices 10B, 10C and 10D are filled vias. The image pickup device 10A has higher thermal resistance than thermal resistance of the circuit devices 10B, 10C and 10D.

Still further, a bonding conductor cannot be disposed immediately below the conformal via unlike with the filled via. Thus, thermal resistance of a path of heat from the bonding conductor 25A to the through electrode 15A is high. In other words, in the image pickup apparatus 1D, heat is less transferred from the intermediate layer 20A to the image pickup device 10A, and thus, particularly, there is no possibility of degradation of image quality or reliability.

As described above, in the image pickup apparatus 1D, the first semiconductor device having the highest thermal resistance among the plurality of semiconductor devices 10A to 10D, and the first layer having the highest thermal resistance among the plurality of intermediate layers 20A to 20C are disposed between the first surface HSA on which the semiconductor circuit 12C that is the first circuit is formed and the front surface 30SA.

However, if in the image pickup apparatus, at least one of the first semiconductor device with the highest thermal resistance among the plurality of semiconductor devices 10A to 10D or the first layer with the highest thermal resistance among the plurality of intermediate layers 20A to 20C is disposed between the first surface HSA on which the semiconductor circuit 12C that is the first circuit is formed and the front surface 30SA, heat is less transferred from the intermediate layer 20A to the image pickup device 10A, and thus, there is no possibility of degradation of image quality or reliability.

Modifications of Second Embodiment

Image pickup apparatuses 1E and 1F of modifications of the second embodiment are similar to the image pickup apparatus 1D, and thus, the same reference numerals will be assigned to components having the same functions, and description will be omitted.

Modification 1 of Second Embodiment

Figure 9:
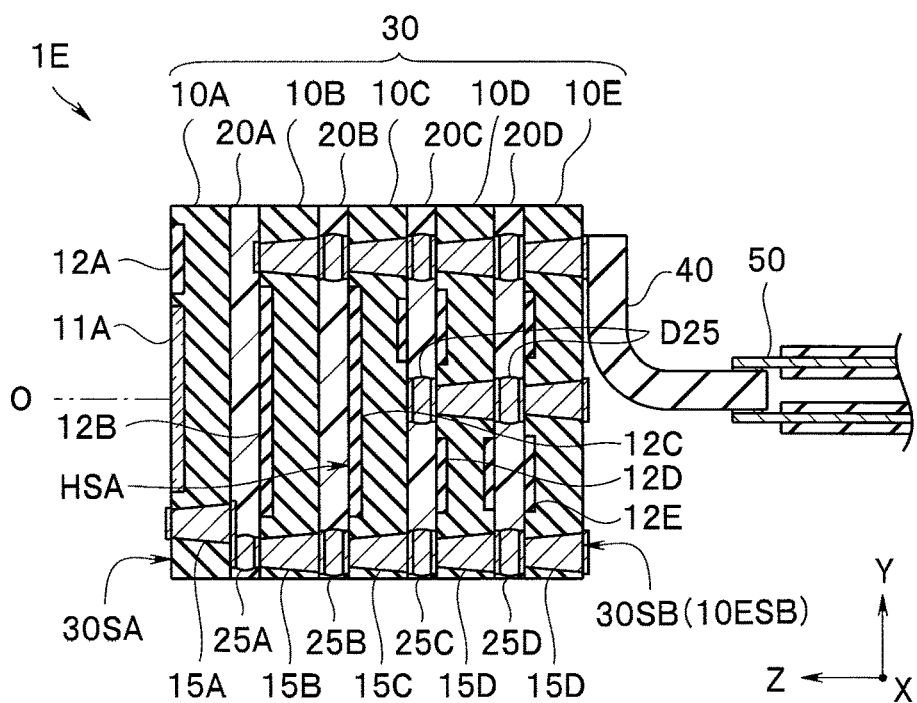
FIG. 9 is a cross-sectional view of an image pickup apparatus of modification 1 of the second embodiment.

The image pickup apparatus 1E of the present modification illustrated in FIG. 9 includes five semiconductor devices 10A to 10E and four intermediate layers 20A to 20D. The semiconductor circuit 12C of the circuit device 10C is the first circuit with the largest heat generation amount.

In the image pickup apparatus 1E, unlike with the image pickup apparatus 1D, the number of the bonding conductors 25A to 25D provided in the intermediate layers 20A to 20D are different. The intermediate layer 20A includes four bonding conductors 25A, and the intermediate layer 20B includes six bonding conductors 25B. The intermediate layers 20C and the intermediate layers 20D include nine bonding conductors 25C and 25D.

While thicknesses of the intermediate layers 20A to 20D are substantially the same, a sum of cross-section areas of the bonding conductors 25A in a cross-section parallel to the front surface 30SA is the smallest in the intermediate layer 20A, and thus, the intermediate layer 20A is the first layer with the highest thermal resistance.

In the image pickup apparatus 1E, heat generated from the semiconductor circuit 12C is less transferred to the image pickup device 10A by the intermediate layer 20A, and thus, there is no possibility of degradation of image quality or reliability.

Note that the intermediate layer may include a dummy bonding conductor (dummy electrode) which has the same configuration as the configuration of the bonding conductor but is not electrically connected to the light reception circuit 11A to reduce thermal resistance. For example, the image pickup apparatus 1E includes a dummy bonding conductor D25.

In other words, when circuit arrangement of the semiconductor devices on a principal surface is designed, if there is a space where a dummy bonding conductor can be disposed also in a region which is difficult to be electrically connected to the light reception circuit 11A, it is preferable to dispose a dummy bonding conductor for the purpose of heat transfer.

Modification 2 of Second Embodiment

Figure 10:
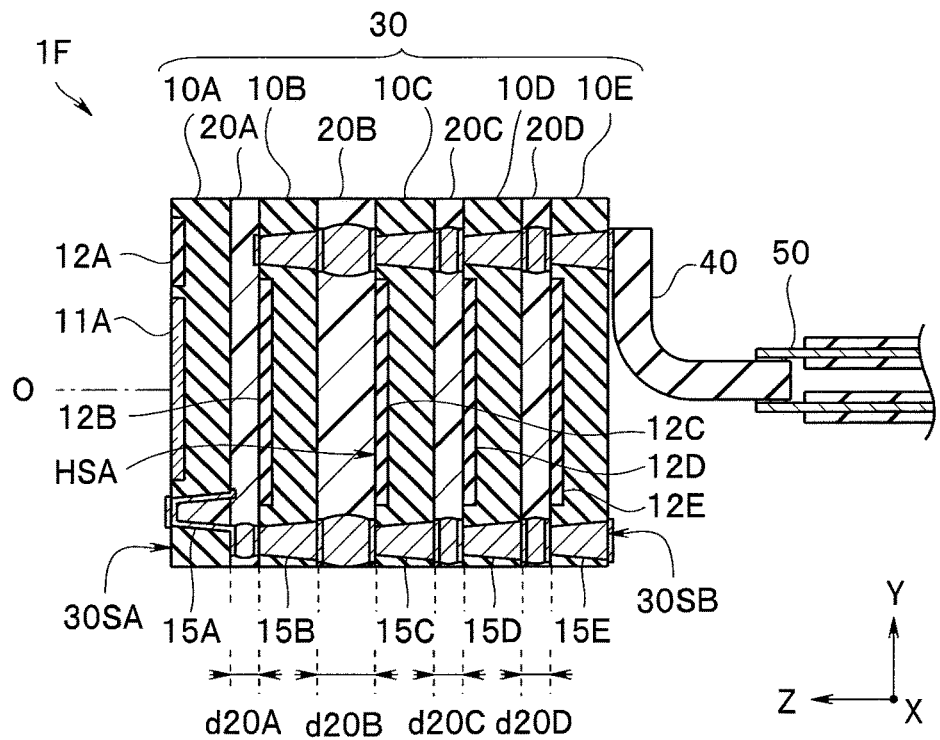
FIG. 10 is a cross-sectional view of an image pickup apparatus of modification 2 of the second embodiment.

In the image pickup apparatus 1F of the present modification illustrated in FIG. 10, the intermediate layer 20B is the first layer with the highest thermal resistance. In other words, a thickness d20B of the intermediate layer 20B is thicker than thicknesses d20A, d20C and d20D of other intermediate layers 20A, 20C and 20D.

In the image pickup apparatus 1F, the intermediate layer 20B that is the first layer which is thickest and has the highest thermal resistance among the plurality of intermediate layers is disposed between the first surface HSA and the front surface 30SA.

In the image pickup apparatus 1F, heat is less transferred from the semiconductor circuit 12C that is the first circuit to the image pickup device 10A by the intermediate layer 20B, and thus, there is no possibility of degradation of image quality or reliability.

If the first layer having at least one of a configuration of the image pickup apparatus 1D in which a thickness of the first layer is over 150% of thicknesses of other intermediate layers, or a configuration of the image pickup apparatus 1E in which a sum of cross-section areas of the bonding conductors included in the first layer is smaller than sums of cross-section areas of the bonding conductors included in other intermediate layers, is disposed between the first surface HSA and the front surface 30SA, there is no possibility of degradation of image quality or reliability.

Note that it is particularly preferable that all the intermediate layers 20A and 20B disposed between the front surface 30SA and the first surface HSA have higher thermal resistance than thermal resistance of all the intermediate layers 20C and 20D disposed between the first surface HSA and the rear surface 30SB, because heat generated from the semiconductor circuit 12C that is the first circuit is more transferred to the wiring board 40 and is less transferred to the light reception circuit 11A.

Further, it is particularly preferable that the intermediate layer 20D that is located closer to the rear surface 30SB out of the intermediate layers 20C and 20D disposed between the first surface HSA and the rear surface 30SB have smaller thermal resistance, because heat generated from the semiconductor circuit 12C that is the first circuit is more transferred to the wiring board 40.

A filler having high heat conductivity may be mixed into resin of the intermediate layer to reduce thermal resistance.

Examples of a non-conductive filler having higher heat conductivity than heat conductivity of resin can include $SiO_2$, SiC, AlN, ZnO, $Si_3N_4$, BN and $Al_2O_3$.

Further, it is preferable that the intermediate layer 20A that is located closer to the front surface 30SA out of the intermediate layers 20A and 20B disposed between the front surface 30SA and the first surface HSA have higher thermal resistance, because heat generated from the semiconductor circuit 12C that is the first circuit is less transferred to the light reception circuit 11A.

Resin including air, for example, equal to or more than 10% by volume may be used to increase thermal resistance of the intermediate layer. Heat conductivity of air is 0.024 W/m·K, which is extremely small, and thus, thermal resistance of resin including air is high.

Note that it goes without saying that it is only necessary that at least one of the first semiconductor device with the highest thermal resistance among the plurality of circuit devices 10B to 10C or the first layer with the highest thermal resistance among the plurality of intermediate layers 20A to 20D be disposed between the first surface HSA on which the semiconductor circuit that is the first circuit is formed and the front surface 30SA.

In other words, the image pickup apparatus may include the first semiconductor device having either one of the configuration in the first embodiment or the configuration in the modifications of the first embodiment and the first layer in either one of the second embodiment or the modifications of the first embodiment.

Third Embodiment

An image pickup apparatus 1G of a third embodiment is similar to the image pickup apparatus 1, or the like, and the same reference numerals will be assigned to components having the same functions, and description will be omitted.

Figure 11A:
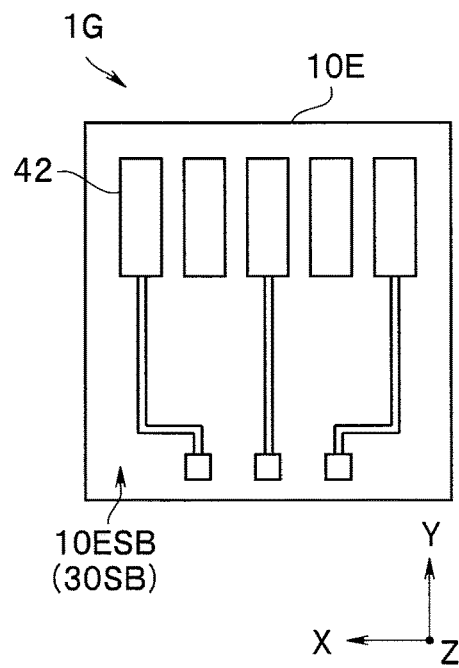
FIG. 11A is a rear view of a circuit device of an image pickup apparatus of a third embodiment.

As illustrated in FIG. 11A, the image pickup apparatus 1G includes the bonding electrodes 42 that are regions to which the wiring board 40 is to be bonded, on a rear surface 10ESB (rear surface 30SB of the stacked device 30) of the circuit device 10E disposed at the rear end of the stacked device 30 including the circuit devices 10B to 10E.

Figure 11B:
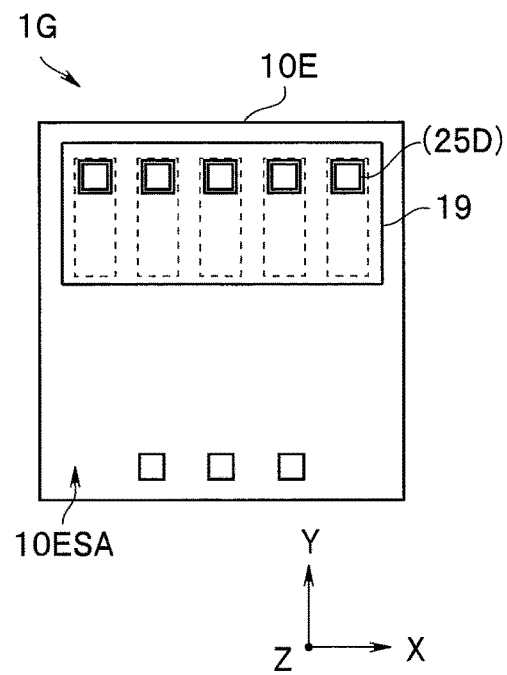
FIG. 11B is a front view of the circuit device of the image pickup apparatus of the third embodiment.

Further, as illustrated in FIG. 11B, a conductive film 19 having a wider area surrounding bonding regions with the bonding conductors 25D of the intermediate layer 20D is disposed on a front surface 10ESA of the circuit device 10E. The conductive film 19 is disposed in an overlapping region that overlaps with regions where the bonding electrodes 42 are disposed on the rear surface 10ESB viewed in an optical axis direction. Thus, a ratio of an area where the conductive film 19 is disposed is higher in the overlapping region than in a region around the overlapping region on the front surface 10ESA.

In other words, the front surface 10ESA of the circuit device WE that is the semiconductor device disposed at the rear end among the plurality of semiconductor devices includes an overlapping region that overlaps with the bonding regions with the wiring board 40 viewed in a stacking direction, and a peripheral region around the overlapping region. Then, a ratio of an area where the conductive film 19 is formed is higher in the overlapping region than in the peripheral region.

By this means, heat generated from the circuit device 10E and heat transferred from other circuit devices to the circuit device 10E are transferred to the wiring board 40 in order of the conductive film 19, the bonding conductors 25D and the bonding electrodes 42. Thus, in the image pickup apparatus 1G, heat generated from the semiconductor circuit 12C is more transferred to the wiring board 40, and thus, there is no possibility of degradation of image quality or reliability.

Fourth Embodiment

An image pickup apparatus 1H of a fourth embodiment is similar to the image pickup apparatus 1, or the like, and thus, the same reference numerals will be assigned to components having the same functions, and description will be omitted.

Figure 12:
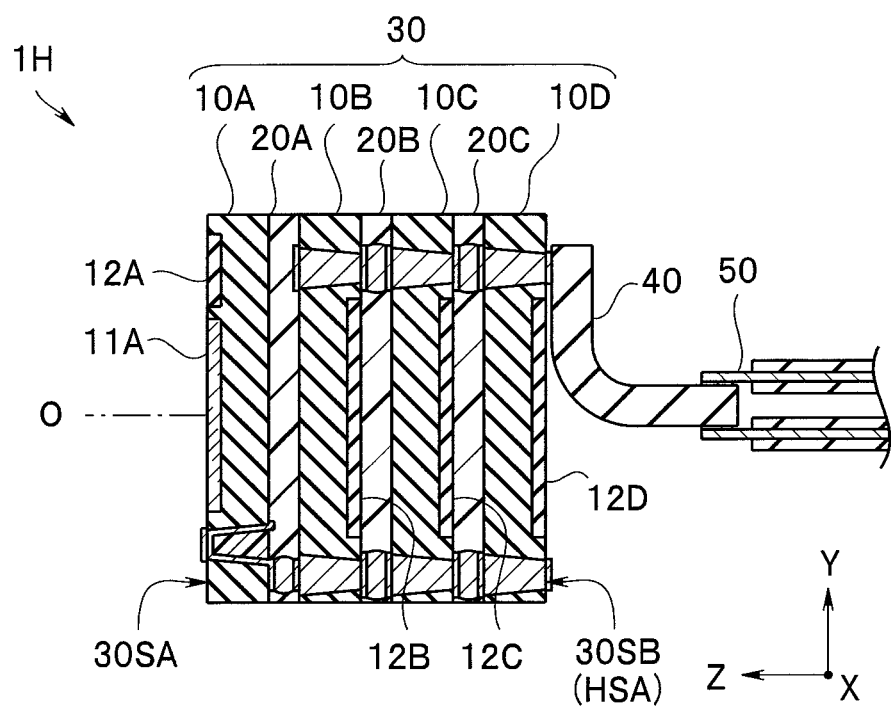
FIG. 12 is a cross-sectional view of an image pickup apparatus of a fourth embodiment.

In the image pickup apparatus 1H illustrated in FIG. 12, the semiconductor circuit 12D of the circuit device 10D having the rear surface 30SB is the first circuit having the largest heat generation amount. Further, the semiconductor circuit 12D is formed on the rear surface 30SB. In other words, the rear surface 30SB is the first surface HSA.

In the image pickup apparatus 1H, heat generated from the semiconductor circuit 12D is more transferred to the wiring board 40 and is less transferred to the light reception circuit 11A. The heat is more transferred to the signal cable 50 by way of the wiring board 40. Thus, in the image pickup apparatus 1H, there is no possibility of degradation of image quality or reliability due to thermal noise.

Note that it goes without saying that the endoscopes 9A to 9H including the image pickup apparatuses 1A to 1H have effects of the respective image pickup apparatuses 1A to 1H in addition to the effects of the endoscope 9. Further, while the image pickup apparatuses 1A to 1H are image pickup apparatuses for endoscopes, application of the image pickup apparatuses of the embodiments is not limited to endoscopes.

The present invention is not limited to the above-described embodiments, and the like, and various changes, modifications, and the like, can be made in a range not changing a gist of the present invention.

What is claimed is:
1. An image pickup apparatus comprising:
a stacked device in which a plurality of semiconductor devices respectively including a plurality of through electrodes are stacked, wherein
the plurality of semiconductor devices include an image sensor and a plurality of circuit devices which are disposed proximally relative to the image sensor in an optical axis direction and in which a plurality of semiconductor circuits are respectively disposed,
a first semiconductor device, among the plurality of semiconductor devices, includes a first through electrode of the plurality of through electrodes in which thermal resistance is highest among the plurality of through electrodes,
a first semiconductor circuit is disposed on the plurality of semiconductor devices other than the first semiconductor device, the first semiconductor circuit having a largest heat generation amount of the plurality of semiconductor circuits,
the first semiconductor device is disposed distally relative to a first surface in the optical axis direction on which the first semiconductor circuit is disposed,
the first through electrode of the first semiconductor device is a conformal via,
the plurality of through electrodes of the plurality of semiconductor devices other than the first semiconductor device are filled vias, and
a cross-section area of conductors of the first through electrode of the first semiconductor device is smaller than a cross-section area of conductors of the plurality of through electrodes of the plurality of semiconductor devices other than the first semiconductor device.

2. The image pickup apparatus according to claim 1, wherein the first semiconductor device is the image sensor.

3. The image pickup apparatus according to claim 1, wherein heat conductivity of a material of conductors of the first through electrode of the first semiconductor device is smaller than heat conductivity of materials of conductors of the plurality of through electrodes of the semiconductor devices other than the first semiconductor device.

4. The image pickup apparatus according to claim 1, wherein a number of the first through electrode of the first semiconductor device is smaller than a number of the plurality of through electrodes of the plurality of semiconductor devices other than the first semiconductor device.

5. The image pickup apparatus according to claim 1, wherein a substrate of the first semiconductor device is thicker than substrates of the plurality of semiconductor devices other than the first semiconductor device.

6. The image pickup apparatus according to claim 1, wherein the first surface is a rear surface of a circuit device of the plurality of circuit devices that includes the first surface.

7. The image pickup apparatus according to claim 1, further comprising:
    a wiring board bonded to a rear surface of the stacked device; and
    a signal cable bonded to the wiring board.

8. The image pickup apparatus according to claim 7, wherein a front surface of a semiconductor device disposed at a rear end, in the optical axis direction, among the plurality of semiconductor devices comprises:
    an overlapping region that overlaps with a bonding region with the wiring board viewed in a stacking direction; and
    a peripheral region outside the overlapping region,
    wherein a ratio of an area wherein a conductive film is formed in the overlapping region is higher than a ratio of an area where the conductive film is formed in the peripheral region.

9. The image pickup apparatus according to claim 1, wherein the first circuit is formed on a rear surface of a semiconductor device disposed at a rear end, in the optical axis direction, among the plurality of semiconductor devices.

10. An endoscope comprising:
    the image pickup apparatus according to claim 1.

11. The image pickup apparatus according to claim 1, further comprising a plurality of intermediate layers each including a bonding conductor, each of the plurality of intermediate layers being disposed between adjacent semiconductor devices of the plurality of semiconductor devices.

12. An image pickup apparatus comprising:
    a stacked device comprising at least two semiconductor devices, the at least two semiconductor devices comprising a first semiconductor device including an image sensor and a second semiconductor device including a first semiconductor circuit,
    a wiring board bonded to a proximal surface of the stacked device; and
    a signal cable bonded to the wiring board,
    wherein the at least two semiconductor devices include a plurality of through electrodes,
    a first through electrode of the plurality of through electrodes is included in the first semiconductor device, a thermal resistance of the first through electrode is highest among the plurality of through electrodes,
    a cross-section area of conductors of the first through electrode of the first semiconductor device is smaller than a cross-section area of conductors of the plurality of through electrodes of the at least two semiconductor devices other than the first semiconductor device; and
    the first semiconductor device is disposed distally relative to a first surface in an optical axis direction on which the first semiconductor circuit is disposed, wherein a front surface of a semiconductor device disposed at a rear end, in the optical axis direction, among the plurality of semiconductor devices comprises:
        an overlapping region that overlaps with a bonding region with the wiring board viewed in a stacking direction of the at least two semiconductor devices; and
        a peripheral region outside the overlapping region,
    wherein a ratio of an area where a conductive film is formed in the overlapping region is higher than a ratio of an area where the conductive film is formed in the peripheral region.

13. The image pickup apparatus according to claim 12, wherein the first through electrode is a conformal via, and the plurality of through electrodes other than the first through electrode are filled vias.

14. The image pickup apparatus according to claim 12, wherein heat conductivity of a material of conductors of the first through electrode of the first semiconductor device is smaller than heat conductivity of materials of conductors of the plurality of through electrodes of the second semiconductor device.

15. The image pickup apparatus according to claim 12, wherein a number of the first through electrode of the first semiconductor device is smaller than a number of the plurality of through electrodes of the second semiconductor device.

* * * * *